United States Patent
Tovey et al.

(10) Patent No.: US 6,416,462 B1
(45) Date of Patent: Jul. 9, 2002

(54) SHEATH AND APPLICATOR FOR SURGICAL INSTRUMENT

(75) Inventors: H. Jonathan Tovey, Monroe, CT (US); Eric C. Miller, Los Gatos, CA (US)

(73) Assignee: Tyco Healthcare Group LP, Norwalk, CT (US)

( * ) Notice: Subject to any disclaimer, the term of this patent is extended or adjusted under 35 U.S.C. 154(b) by 0 days.

(21) Appl. No.: 09/487,093

(22) Filed: Jan. 19, 2000

Related U.S. Application Data

(60) Provisional application No. 60/116,272, filed on Jan. 19, 1999.

(51) Int. Cl.$^7$ ................................................. A61B 1/04
(52) U.S. Cl. ........................ 600/121; 600/124; 600/125; 206/363
(58) Field of Search ................................ 600/121, 124, 600/125; 206/363, 438

(56) References Cited

U.S. PATENT DOCUMENTS

| | | | | |
|---|---|---|---|---|
| 4,914,521 A | * | 4/1990 | Adair | ........................ 358/229 |
| 5,088,178 A | | 2/1992 | Stolk | |
| 5,325,846 A | | 7/1994 | Linvatec | |
| 5,355,886 A | | 10/1994 | Dominguez et al. | |
| 5,429,118 A | * | 7/1995 | Cole et al. | .................. 600/121 |
| 5,433,221 A | * | 7/1995 | Adair | ........................ 128/849 |
| 5,569,159 A | * | 10/1996 | Anderson et al. | ........... 600/114 |
| 5,569,161 A | * | 10/1996 | Ebling et al. | ................ 600/121 |
| 5,971,916 A | * | 10/1999 | Koren | ........................ 600/122 |

FOREIGN PATENT DOCUMENTS

NL        1 001 251 C       3/1997

* cited by examiner

Primary Examiner—Linda C. M. Dvorak
Assistant Examiner—Jocelyn Ram

(57) ABSTRACT

A sterile sheath and applicator apparatus for use with a surgical instrument, includes a flexible sheath member defining a longitudinal bore at least extending through the proximal end thereof dimensioned for reception of an elongated portion of a surgical instrument and an applicator mounted adjacent the proximal end of the sheath member for facilitating positioning of the sheath member about the elongated portion of the surgical instrument. The applicator includes a hollow tube portion defining an axial bore therethrough and a handle operatively connected to the tube portion. The tube portion is sufficient in length to support the sheath member in a folded condition thereof with a major portion of the length of the sheath member disposed about the tubular portion. The handle is dimensioned to be engaged by a surgeon and manipulated to extend the sheath member about the elongated portion of the instrument to an extended position with the elongated portion at least partially received within the longitudinal bore of the sheath member.

13 Claims, 5 Drawing Sheets

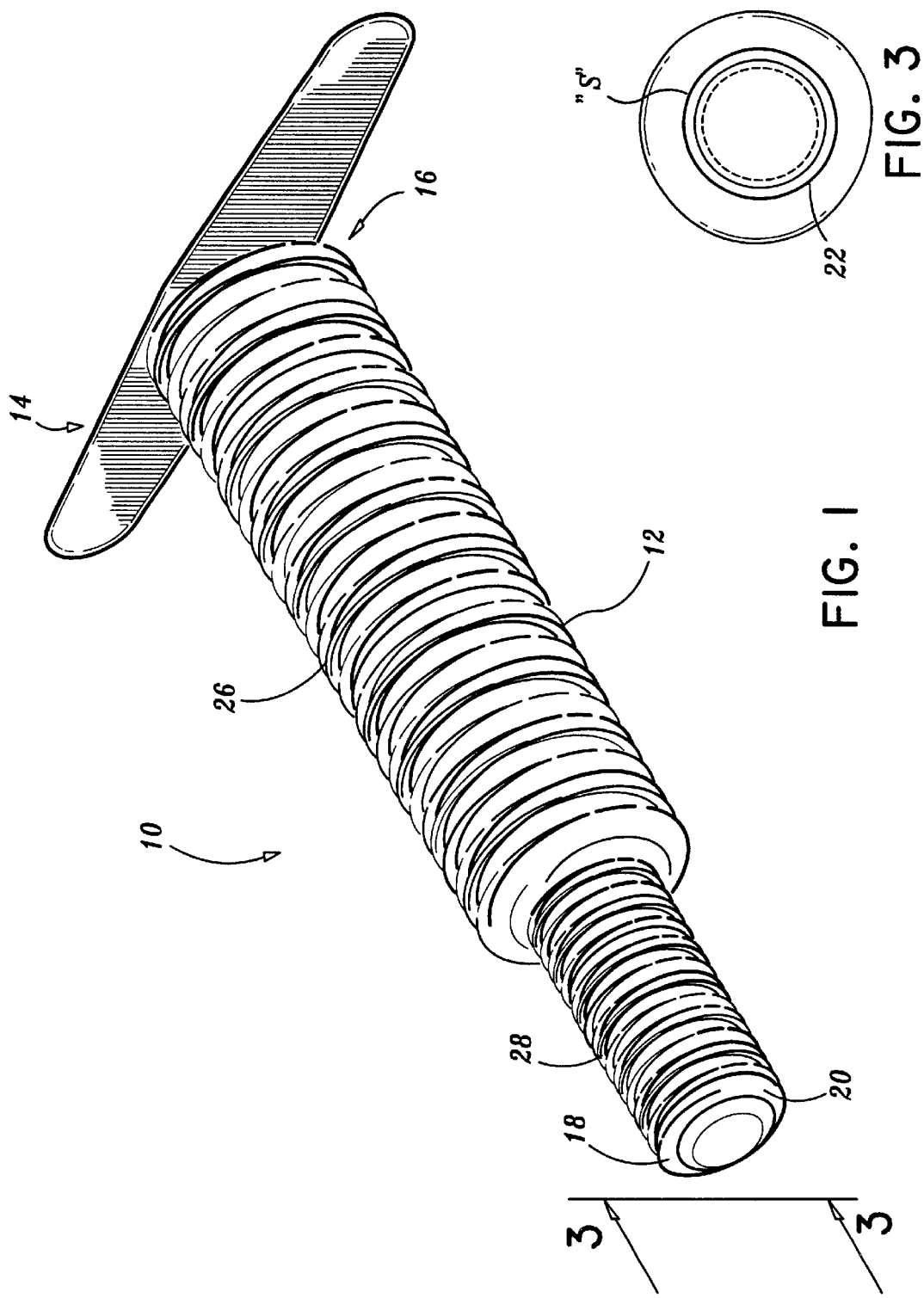

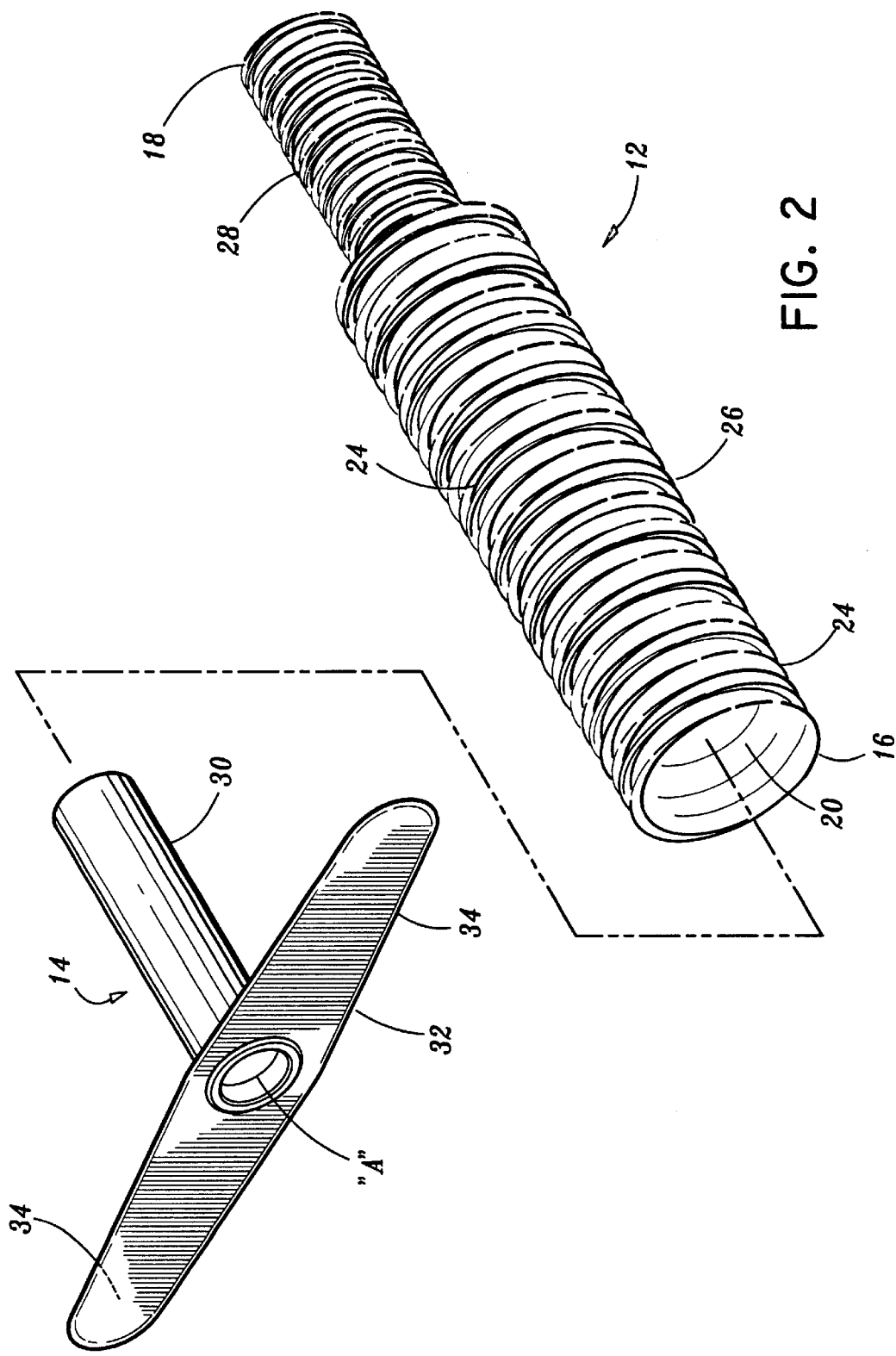

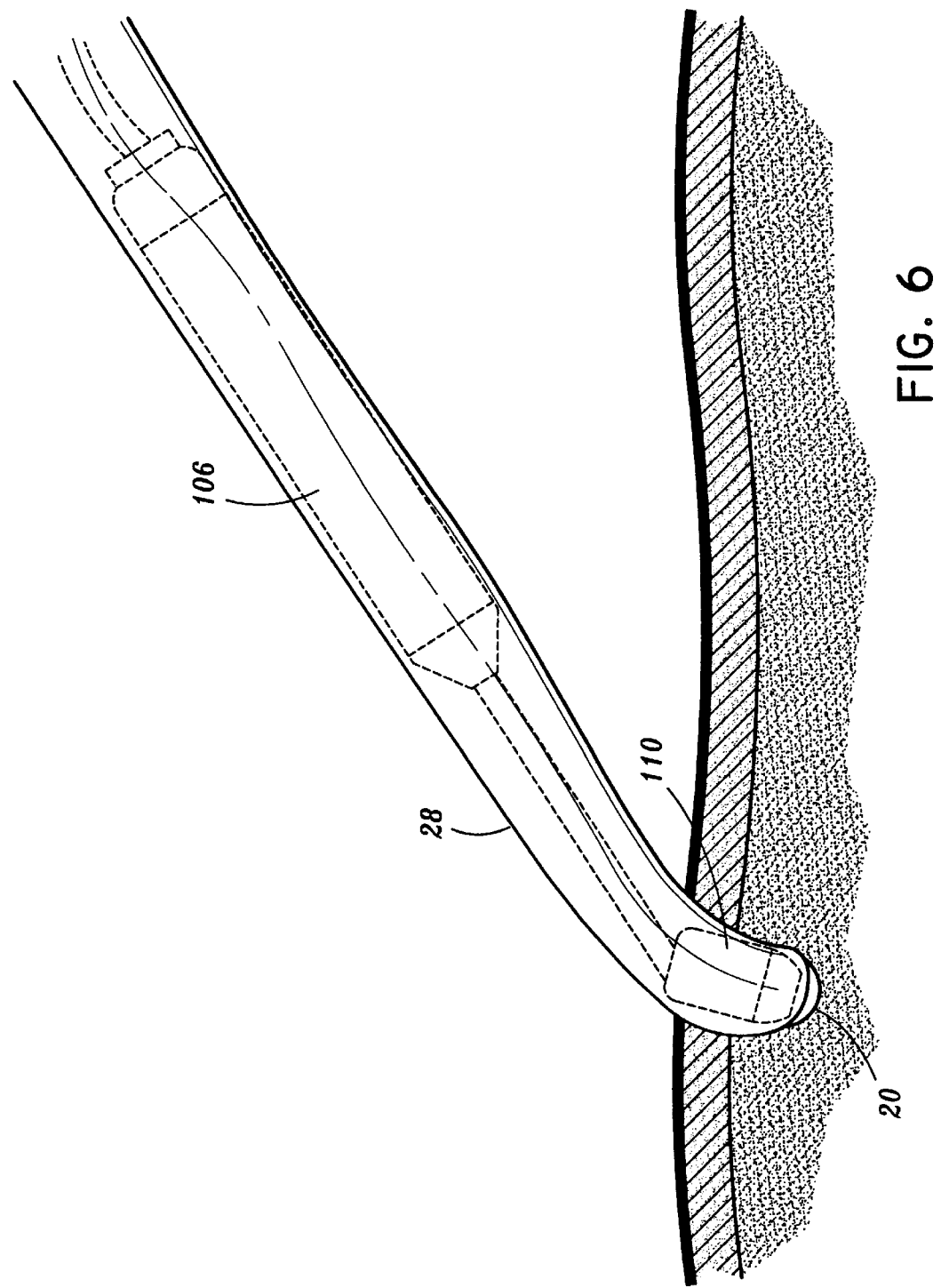

SHEATH AND APPLICATOR FOR SURGICAL INSTRUMENT

This Appln claims bebnefit of Prov. No. 60/116,272 filed Jan. 19, 1999.

BACKGROUND

1. Field of the Disclosure

The present disclosure relates to a sheath apparatus for positioning about a surgical instrument, and, in particular, to a disposable sheath and associated applicator for use with a radiation monitoring probe to preserve the sterility of the probe while performing diagnosis.

2. Description of the Related Art

Sheath apparatuses for maintaining the sterility of surgical instruments are well known in the art, particularly, in the field of endoscopy. For example, U.S. Pat. No. 4,878,485 to Adair discloses an endoscopic sheath including a rigid cylindrical housing for receiving the elongated endoscopic portion of an endoscope and a folded sleeve mounted adjacent the proximal end of the housing. The sleeve is extendable to cover the housing and the endoscope so as to prevent contamination of the endoscope during use. Other sheath apparatii having endoscopic application are disclosed in U.S. Pat. Nos. 4,852,551 to Opie; 4,869,238 to Opie; and 5,402,768 to Adair.

The above-described conventional sheath apparatii are suitable for their intended purposes in preserving the sterility of reusable endoscopes; however, these apparatii are deficient in certain respects, which deficiencies detract from their overall effectiveness and adaptability, particularly, for radiation monitoring probe instruments. Radiation monitoring probe instruments are utilized for detection of radioactively tagged (i.e., with radiopharmaceuticals) tissue for tissue diagnosis purposes. By way of example, one commercially available radiation monitoring probe is the RMD Gamma Guidance System manufactured by Radiation Monitoring Devices (RMD), Inc. of Watertown, Mass. This system includes a control unit and a probe for localizing and quantifying regions of increased radiopharmaceutical uptake in tissue. The probe generally includes a narrow shaft portion having an enlarged distal head which houses the electrical detection components for tissue diagnosis. An electrical cable connects the probe to the control unit. To date, there exists no sheath apparatus suitable for use with a radiation monitoring probe system of the afore described type.

SUMMARY

Accordingly, the present disclosure relates to a sheath and associated applicator apparatus particularly adapted to be mounted to a radiation detection probe to preserve the probe from contamination fluids during use in diagnostic procedures thereby precluding the need to sterilize the probe components after each use. Generally, the sheath and applicator apparatus includes a flexible sheath member defining a longitudinal bore at least extending through the proximal end thereof dimensioned for reception of an elongated portion of a surgical instrument and an applicator mounted adjacent the proximal end of the sheath member for facilitating positioning of the sheath member about the elongated portion of the surgical instrument. The applicator includes a hollow tube portion defining an axial bore therethrough and a handle operatively connected to the tube portion. The tube portion is sufficient in length to support the sheath member in a folded condition thereof with a major portion of the length of the sheath member disposed about the tubular portion. The handle is dimensioned to be engaged by a surgeon and manipulated to extend the sheath member about the elongated portion of the instrument to an extended position with the elongated portion at least partially received within the longitudinal bore of the sheath member. Preferably, the sheath member defines an accordion configuration along a portion of its length to facilitate folding and positioning of the sheath member to the folded condition thereof supported by the applicator.

In a preferred embodiment, the sheath member defines a protruding distal tip portion with the distal tip portion defining a closed distal end face. The distal end face preferably has a generally smooth outer surface with no folds, creases, etc. to facilitate transmission of signals to and from the instrument. The sheath member may include a first proximal portion and a second distal portion with the first proximal portion defining a diameter greater than a diameter of the second distal portion. In the mounted position of the sheath member, the first proximal portion loses the cable extending to the probe while the second distal portion encloses the probe.

BRIEF DESCRIPTION OF THE DRAWINGS

Preferred embodiments of the disclosure are described with reference to the drawings, wherein;

FIG. 1 is a perspective view illustrating the sheath and applicator apparatus in accordance with the principles of the present disclosure;

FIG. 2 is a perspective view with parts separated illustrating the flexible sheath member and the applicator of the apparatus of FIG. 1;

FIG. 3 is an end view of the apparatus taken along the lines 3—3 of FIG. 1;

FIG. 6 is a view illustrating positioning of the radiation monitoring probe with mounted apparatus within tissue for diagnostic purposes.

DETAILED DESCRIPTION OF THE PREFERRED EMBODIMENTS

Figure 4:
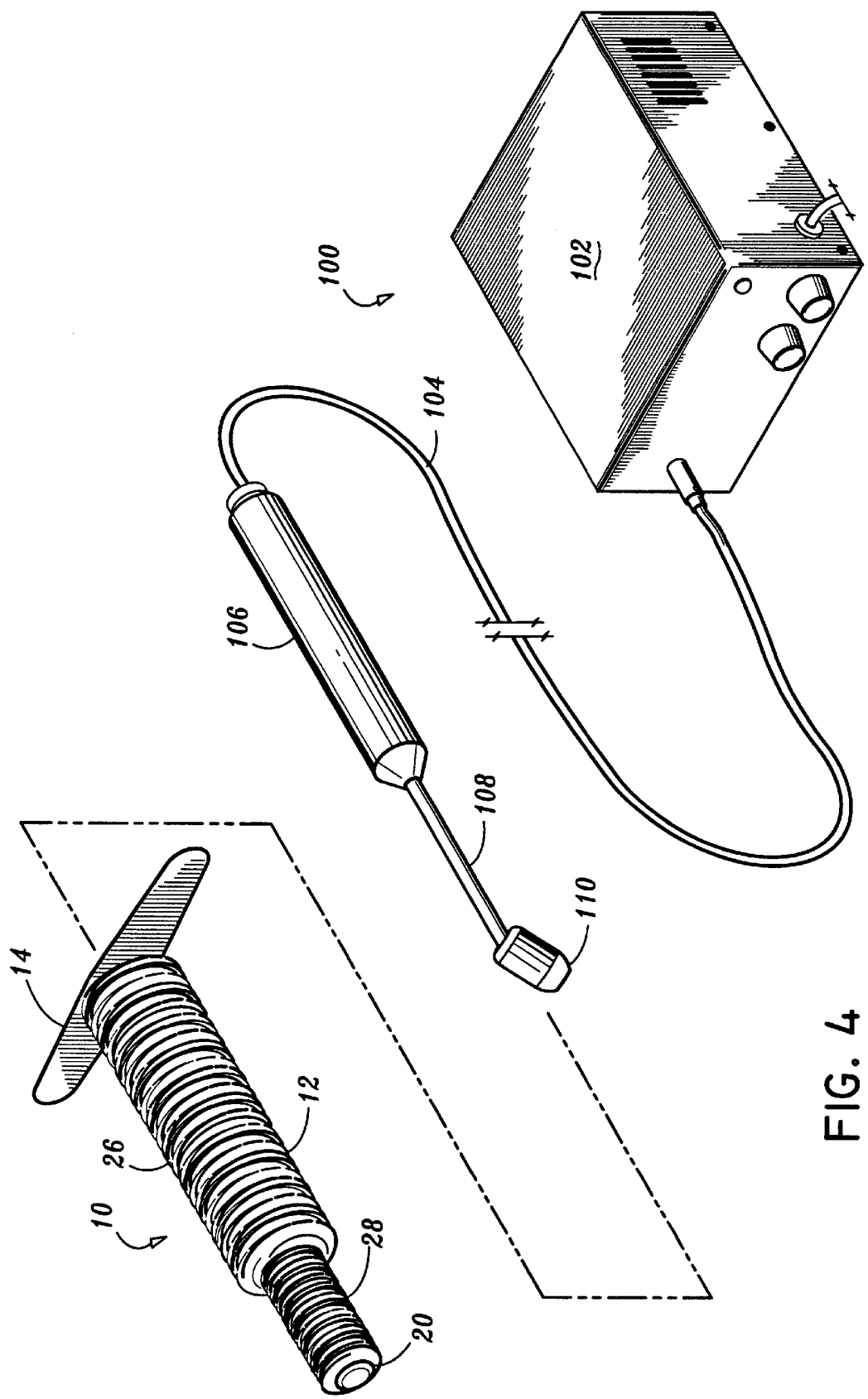
FIG. 4 is a perspective view of the RMD Gamma Guidance System and the apparatus of FIG. 1 prior to mounting of the apparatus about the radiation monitoring probe and cable.

Referring now to the drawings wherein like reference numerals identify similar or like reference elements through the several views, the sheath and applicator apparatus in accordance with the principles of the present disclosure is illustrated. Apparatus 10 is intended for use with a radiation monitoring probe, particularly, the probe of the RMD Gamma Guidance System manufactured by Radiation Monitoring Devices (RMD), Inc. of Watertown, Mass. However, it is to be appreciated that the apparatus 10 has application with other surgical instruments, particularly, any minimally invasive instrument intended for reuse, including endoscopes, laparoscopes, arthroscopes, colonoscopes, etc.

With references now to FIGS. 1–3 apparatus 10 generally includes two components, namely, elongated flexible sheath member 12 and applicator 14 which is connected to the sheath member 12. Sheath member 12 is a drape or condom fabricated from a suitable biocompatible polymeric material, preferably, a polyurethane. Sheath member 12 has proximal end 16, distal end 18 and defines a longitudinal opening 19 extending between the proximal and distal ends 16, 18. Proximal end 16 is open to permit positioning of sheath member 12 over the probe. Distal end 18 of sheath member 12 is generally closed and defmes a form fitting tip 20 which fits onto the probe tip. Form fitting tip 20 generally protrudes outwardly relative to the distal end 18 of sheath member 12 to generally correspond to the distal configuration of the probe. Form fitting tip 20 further defines a distal inner window 22 extending generally transversely to the longitudinal axis of sheath member 12. Window 22 is clear possessing no seams, fold lines, etc. and preferably has a planar outer surface so as to facilitate transmission and reception of any signals or to and from the tissue.

Sheath member 12 has an accordion characteristic at least along a major portion of the length of the sheath member 12. The accordion configuration is characterized by having a plurality of fold lines, creases 24 etc. which permit sleeve member 12 to fold upon itself to assume the accordion or mounted arrangement depicted in FIG. 1 to thereby facilitate storage and positioning of the sheath member 12 relative to applicator 12. Sheath member 12 further possesses proximal end portion 26 and distal end portion 28. Proximal end portion 26 defines a diameter which is greater than the diameter of the distal end portion 28 of the sheath member 12. With this arrangement and in the mounted condition of sheath member 12 relative to the probe, proximal end portion 26 is advantageously configured to enclose the cable connecting the probe to the control unit, and distal end portion 28 is advantageously configured to enclose the probe.

The geometrical characteristics of sheath member 12 are as follows:

1) overall length in extended condition ranges from about 80 inches to about 112 inches, preferably about 96 inches, with the length of proximal end portion 26 ranging from about 80 to about 94 inches and the length of distal end portion 28 ranging from about 6 to 12 inches.

2) overall length in stored condition ranging from about 4 inches to about 6 inches.

3) the diameter of proximal end portion 26 ranging from about 2 inches to about 3 inches and the diameter of distal end portion 28 ranging from about 1 inches to about 2 inches.

Sheath member 12 may be manufactured by an extrusion process to form a tube-like configuration of the entire sheath member 12 . In this method of manufacture, distal inner window 22 may be secured to distal end 18 of sheath member 12 via conventional heat sealing techniques along a seal line "s" shown in FIG. 3. In an alternate method of manufacture, sheath member 12 may be formed as a flat sheet of polyurethane, cut and rolled to the desired tube configuration, and, thereafter, heat sealed along its longitudinal edges. Window 22 may be secured via heat sealing or any other suitable manner.

With reference now to FIGS. 1–2, applicator 14 will be discussed in detail. Applicator 14 is intended to 1) facilitate positioning of the apparatus 10 onto the instrument; and 2) to support the folded sheath member 12 during storage. Applicator 14 includes tubular portion 30 and handle 32 connected to the proximal end of the tubular portion 30. Tubular portion 30 is preferably rigid to support the folded flexible sheath member 12 during storage and during positioning on the probe. Tubular portion 30 defines an axial bore 35 dimensioned to receive the probe. Handle 32 includes first and second handle portions 34 disposed in diametrical opposed relation and advantageously dimensioned to be engaged by the user. Handle 32 facilitates placement of apparatus 10 about the instrument. In a preferred embodiment, handle 32 is rigid. Alternatively, it is envisioned that handle 32 may be relatively flexible. In accordance with this embodiment, handle portions 34 may be wrapped about the probe subsequent to placement to mount the applicator 14 to the probe. Handle portions 34 may each include a locking slit 36 (shown in phantom in FIG. 1) which cooperates with the locking slit 36 of the other handle portion 34 to secure the handle portions 34 to each other and to the surgical instrument about which it is wrapped thereby positively mounting applicator 14 to the instrument. It is envisioned that other means for securing handle portions 34 are contemplated including adhesives, locking couplers, etc.

As depicted in FIG. 1, in the folded or stored configuration, tubular portion 30 of applicator 14 supports a major portion of the length of the folded sheath member 12. preferably, the entire length of the sheath member 12.

Figure 5:
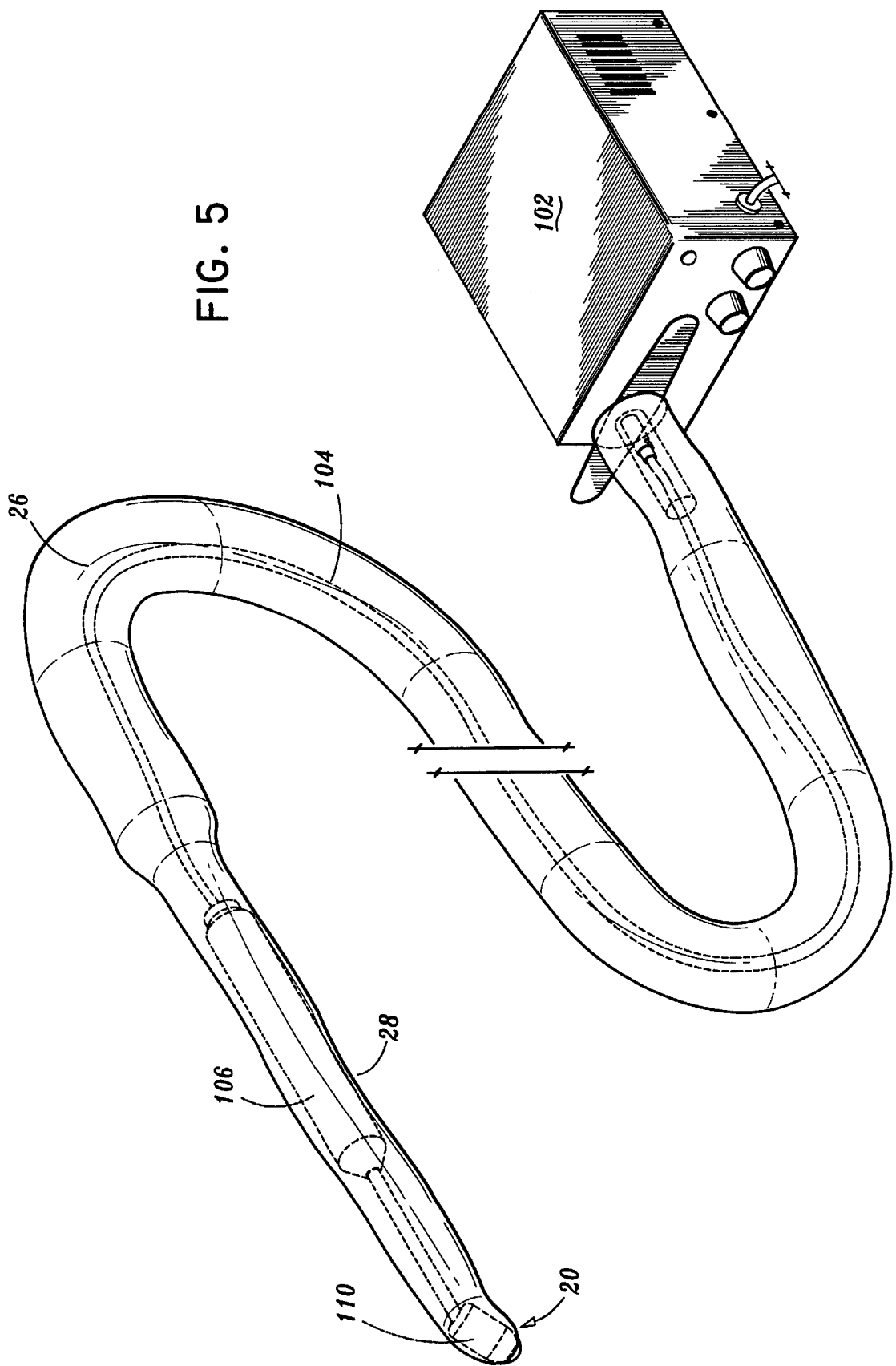
FIG. 5 is a perspective view illustrating the apparatus positioned on the radiation monitoring probe and the cable of the RMD Gamma Guidance System.

With reference now to FIG. 4, the RMD Gamma Guidance System is illustrated with the sheath apparatus 10 shown prior to installation. As shown and briefly discussed hereinabove, the system 100 includes a control unit 102, a probe 104 and a cable 106 interconnecting the probe with the control unit 102. The probe 104 possesses a narrow shaft portion 108 having an enlarged distal head 110 which houses the electrical detection components for detection and quantifying regions of radiopharmaceutical uptake in tissue. With reference now to FIG. 5, to mount sheath apparatus 10 relative to the Guidance System 100, applicator 14 with sheath member 12 in the stored configuration is positioned on probe 104 through grasping and manipulation of handle 32 of the applicator 14. Thereafter, handle 32 is slid over the probe 104 and along the cable 106 to a position adjacent and preferably abutting the control unit 102. During such advancement, sheath member 12 readily unwraps to assume the extended condition depicted in FIG. 5. As appreciated, sheath member 12 is of sufficient length to cover the entire probe and cable with the proximal end portion 26 of the sheath member 12 enclosing the cable 106 and the distal end portion 28 enclosing the probe 104. Furthermore, in the mounted condition of sheath member 12, distal form fitting 20 of the sheath member 12 at least partially accommodates the enlarged distal head 110 of the probe 104 with the distal inner window 22 in proper transverse orientation with respect to the probe end.

FIG. 6 illustrates use of the apparatus 10 in the mounted position relative to the RMD probe in performing tissue diagnosis. As shown, during the procedure, probe 104 and cable 106 are isolated from the surgical environment by the apparatus 10 during the entire procedure. Subsequent to use, apparatus 10 may be removed by sliding the applicator 14 over the cable 106 and probe 104, and then disposed. In that apparatus 10 maintains the sterility of the components of the guidance system 100, steril izati on is not required prior to the next use of the RMD system.

While the invention has been particularly shown and described with reference to certain preferred embodiments, it will be understood by those skilled in the art that various modifications in form and detail may be made therein without departing from the scope and spirit of the invention. Accordingly, modification to the preferred embodiments will be readily apparent to those skilled in the art, and the generic principles defined herein may be applied to other embodiments without departing from the spirit and scope of the invention. Thus, the present invention is not intended to be limited to the embodiments shown, but it is to be accorded the widest scope consistent with the principles and features disclosed herein.

What is claimed is:

1. A sterile sheath and applicator apparatus for use with a surgical instrument, which comprises: a flexible sheath member including proximal and distal ends, and defining a longitudinal axis, the sheath member having a longitudinal bore and being dimensioned to receive a portion of a surgical instrument thereby forming a sterile barrier around the surgical instrument; and an applicator mounted to the proximal end of the sheath member for facilitating position of the sheath member about the surgical instrument, the applicator including a hollow tube portion defining an axial bore therethrough and a handle connected to the tube portion, the tube portion sufficient in length to support the sheath member in a folded condition thereof with a substantial portion of the length of the sheath member disposed about the tubular portion, wherein the handle includes first and second handle portions, the handle portion having sufficient flexibility to be at least partially wrapped about the instrument.

2. An apparatus according to claim 1 wherein the sheath member has accordion-type pleats along a portion of its length to facilitate folding and positioning of the sheath member to be supported by the applicator in said folded condition.

3. An apparatus according to claim 2, wherein the sheath member defines a protruding distal tip portion.

4. An apparatus according to claim 3, wherein the distal tip portion of the sheath member defines a closed distal end face.

5. An apparatus according to claim 4, wherein the distal end face defines a generally smooth outer surface to facilitate transmission of signals to and from the instrument.

6. An apparatus according to claim 5, wherein the sheath member includes a first proximal portion and a second distal portion, the first proximal portion defining a diameter greater then a diameter of the second distal portion.

7. An apparatus according to claim 6, wherein the sheath member defines a length ranging from about 80 inches to about 112 inches.

8. An apparatus according to claim 7, wherein the first proximal portion of the sheath member defines a length ranging from about 80 inches to about 94 inches and wherein the second distal portion of the sheath member defines a length ranging from about 6 inches to about 12 inches.

9. An apparatus according to claim 1, wherein the first and second handle portions each include locking structure to releasably secure the handle portions to each other to facilitate mounting of the applicator to the instrument.

10. An apparatus according to claim 2 further including a surgical instrument, the surgical instrument positionable within the longitudinal bore of the sheath member.

11. An apparatus according to claim 10 wherein the surgical instrument is a radiation monitoring probe.

12. A method of applying a sterile sheath to a surgical instrument thereby forming a sterile shield around said instrument, said method comprising:

providing an elongated, flexible sheath having an opening therethrough and a series of pleats such that, when said pleats are folded, said sheath is in a retracted state;

providing an elongated applicator in said opening to support at least a portion of said sheath in said retracted state; and inserting said surgical instrument into said sheath; and manipulating said applicator to extend said sheath over said surgical instrument such that said sheath is in an elongated state; and securing handle portions of said applicator about said surgical instrument.

13. A method according to claim 12, wherein said surgical instrument is a radiation monitoring probe.

* * * * *